United States Patent [19]

Newman et al.

[11] Patent Number: 4,515,805

[45] Date of Patent: May 7, 1985

[54] SOLUBLE SODIUM CROMOGLYCATE COMPOSITIONS

[75] Inventors: Peter M. Newman, Keyworth; Anthony W. Jenkins, Loughborough, both of England

[73] Assignee: Fisons plc, Ipswich, England

[21] Appl. No.: 515,608

[22] Filed: Jul. 21, 1983

Related U.S. Application Data

[63] Continuation of Ser. No. 315,958, Oct. 28, 1981, abandoned.

[30] Foreign Application Priority Data

Nov. 5, 1980 [GB] United Kingdom ............... 8035457

[51] Int. Cl.³ ............................................. A61K 31/35
[52] U.S. Cl. .................................................. 514/460
[58] Field of Search .......................................... 424/283

[56] References Cited

FOREIGN PATENT DOCUMENTS 1242211 8/1971 United Kingdom .
1381872 1/1975 United Kingdom .
1410588 10/1975 United Kingdom .
1423985 2/1976 United Kingdom .
1549229 7/1979 United Kingdom .

OTHER PUBLICATIONS

Remington's Pharmaceutical Sciences, 16th ed., 1980, pp. 1237, 1261 and 1262.
Chemical Abstracts, 82:160250C (Ito et al.), 1975.

*Primary Examiner*—Leonard Schenkman
*Attorney, Agent, or Firm*—Marshall, O'Toole, Gerstein, Murray & Bicknell

[57] ABSTRACT

There is described a mixture of sodium cromoglycate of mass median diameter from 2 to 30 microns with a pharmaceutically acceptable water soluble carrier of sieve size from 200 to 1000 microns, the carrier having a solubility of greater than 1 to 5 by weight in water at 20° C.

The mixture is useful in the treament of conditions of the gastrointestinal tract.

10 Claims, No Drawings

SOLUBLE SODIUM CROMOGLYCATE COMPOSITIONS

This is a continuation of application Ser. No. 315,958, filed Oct. 28, 1981, now abandoned.

This invention relates to a new pharmaceutical formulation.

Sodium cromoglycate is well known to be useful, when administered by inhalation, for the treatment of asthma. For this use a dry powder mixture is sold comprising fine particles of the drug and coarser (30–80 micron) particles of lactose in a 1:1 weight ratio. This formulation has a slightly bitter taste. The objective in this formulation is to provide a composition in which the particles of drug adhere to the coarse lactose, but are capable of being shaken off the lactose in the airstream which is inhaled by the patient. This formulation is more fully described in British Patent Specification No. 1,242,211. A modification of this powder formulation in which the particle size of the lactose carrier is from 80 to 150 microns in size is disclosed in British Patent Specification No. 1,381,872 and a further modification in which the particle size of the drug is from 2 to 4 microns is disclosed in British Patent Specification No. 1,410,588.

Sodium cromoglycate has also been known for many years, e.g. from British Patent Specification No. 1,423,985, to be useful for the treatment of conditions of the gastro-intestinal tract. Various formulations have been suggested for this use including hard, dense granules of the drug, (as described in British Patent Specification No. 1,549,229), which have been put up in a capsule which is designed to be swallowed. These granules can also be removed from the capsule and dissolved in water. However it has been found that the granules are slow to dissolve, and it has been found necessary to follow the tedious procedure of dissolving them in hot water to ensure complete dissolution, and then to dilute the resulting solution with cold water. Adding sodium cromoglycate powder directly to cold water results in dry, unwetted powder being trapped in a gel of dissolving sodium cromoglycate, and, in consequence, solution time is prolonged because of inadequate wetting/de-aeration. Food allergy is thought to start in the mouth, and the physicochemical properties of sodium cromoglycate, in relation to the anatomy and biochemical conditions of the gastro-intestinal tract, therefore indicate that it should be taken by the patient as a solution for maximum therapeutic benefit. These liquid formulations are prima facie attractive. However multidose liquid formulations inevitably require the inclusion of preservative substances which are undesirable in the treatment of the allergic conditions. Many of the conventionally used preservatives are chemically incompatible with sodium cromoglycate and the limited range of compatible substances have allergenic potential for the group of patients to be treated. On the other hand unit dose liquid forms of drugs are expensive, and are technically very difficult to produce, especially when formulated aseptically without a preservative. Indeed we are unaware of any unpreserved liquid unit dose drug formulation being available commercially. Furthermore liquid dosage forms of all kinds are expensive to transport and store because of their high volume and weight per unit dose.

Tablets containing the drug have been contemplated, but tablet formulations contain excipients, which, as with the preservatives conventionally used in solutions, tend to be allergenic. Furthermore tablets tend to take a long time to dissolve and are therefore inconvenient to the patient.

As a finely divided powder, which is a primary requisite for rapid dissolution, sodium cromoglycate is cohesive, and in pure form aggregates into a gel-like mass in contact with water, especially in cold drinking water.

We have now found, however, that certain therapeutically acceptable carrier materials, classified into particular sized particles, have the property of forming a uniform surface coating of sodium cromoglycate, even in the absence of binding agents. The resulting mixture is free flowing with a uniform distribution of the drug and has the particular advantage that it dissolves rapidly and completely in cold water. Furthermore the formulation can be readily filled into unit dose containers, e.g. sachets, whereby it can be protected from the damaging effects of atmospheric moisture.

This product form has the advantage that it is cheap to produce and distribute, it maximises the drug's bioavailability with the minimum of inconvenience to the patient, and by using a non-allergenic excipient it minimises the chance of any allergic response to the formulation itself. A particular advantage of the formulation is that by selecting a sweet-tasting carrier substance, the unpleasant taste of sodium cromoglycate can be masked acceptably without the need for an artificial flavouring agent. This is of particular value in the treatment of food allergic disease in children where the exclusion of artificial flavours in the diet is a pre-requisite of treatment and where, as with all patients, good compliance with the prescribed drug therapy is as difficult to achieve as it is essential.

As can be appreciated from the considerations set out above the pharmaceutical criteria which are applicable to oral and inhalation forms of the drug are entirely different, and indeed the medical conditions treated by the two different forms of the drug are dealt with by quite separate groups of medical specialist.

Thus, according to the invention we provide a mixture of sodium cromoglycate of mass median diameter from 2 to 30 microns with a pharmaceutically acceptable water soluble carrier of sieve size from 200 to 1000 microns, the carrier having a solubility of greater than 1 to 5 by weight of water at 20° C.

The finely divided sodium cromoglycate preferably has a mass median diameter of from 2 to 10 microns, and more preferably from 3 to 6 microns with 90% of the particles being of less than 30 microns diameter. The particle size of the sodium cromoglycate when below 10 microns may be measured by means of a Coulter counter. When above 10 microns the particle size may be measured by sieving.

The water soluble carrier preferably has a particle size of from 200 to 500 microns, e.g. a mean size of from 270 to 370 microns. The particle size of the water soluble carrier may be measured by sieving.

The water soluble carrier is preferably a sugar, for example xylitol and even more preferably sucrose, e.g. beet sucrose. We naturally prefer to avoid sugars which are poorly absorbed and which can, in certain circumstances, cause diarrhoea. We also prefer the sugar to be in a form which will dissolve quickly in water.

The water soluble carrier preferably has a solubility of greater than 1 to 4 more preferably greater than 1 to 2 and most preferably greater than 1 to 1.5, by weight in water at 20° C.

Sucrose is a particularly acceptable excipient for the formulation since it combines in one substance the merits of ready availability in appropriate size grades, cheapness, the desired physical characteristics for coating with the drug, good crystal strength with a rapid aqueous dissolution rate, freedom from allergenic potential, and a degree of sweetness appropriate to mask the taste of sodium cromoglycate in proportions which are pharmaceutically and medically acceptable. In addition it has a low moisture content and with the crystal size selected does not aggregate either in manufacture or storage.

When the formulation is added to cold water the coated carrier, e.g. sucrose particles, remain separate during the dissolution process and this ensures that the individual particles of sodium cromoglycate are uniformly wetted, thus promoting rapid drug dissolution without gelling.

Other sugars may be used in place of sucrose, but many have disadvantages. Thus glucose has a negative heat of solution which militates against ease of dissolution, lactose is insufficiently water soluble nor is it very sweet and, because of its origins, may contain allergic impurities, and xylitol is expensive and is not readily available in the desired particle size.

We prefer the composition to contain an excess, e.g. a 2 to 20 times, and preferabliy a 4 to 15 times by weight excess, of the water soluble carrier, e.g. sugar, and especially just sufficient sugar to mask the taste of the sodium cromoglycate. The proportion of sugar will thus depend on the particular sugar used. However, we have found that with sucrose a suitable proportion is from 5 to 12, and especially from 7.5 to 10 parts by weight for each part by weight of sodium cromoglycate.

The formulation may be put up into unit dosages, e.g. sachets (which are preferably made of material which will prevent the ingress of water) containing from 50 to 300 mg, e.g. 100 or 200 mg, of sodium cromoglycate and from 1–3 g, e.g. about 2 g, of sugar. The unit doses may be administered from 1 to 6 times a day, preferably before, e.g. about 30 minutes before meals. The composition preferably contains a low proportion of 'heavy metal ions', as we have found that the presence of such ions tends to produce cloudy solutions when the composition is dissolved in water. By the term 'heavy metal ions' we mean ions of metals in groups IIa, Ib, IIb, IIIa, IVa and IVb of the periodic table and of the transition metals. Specific 'metal ions' which are detrimental, in excessive concentrations (i.e. above about 20 ppm) in solutions made up from the compositions of the invention, are $Pb^{++}$, $Ca^{++}$, $Mg^{++}$ and in particular $Fe^{++}$, $Fe^{+++}$ and $Zn^{++}$ ions. We particularly prefer to keep the concentration of $Mg^{++}$ ions as low as possible, e.g. less than about 0.22 p.p.m.

The composition also preferably contains a low proportion of water, e.g. less than 2%, preferably less than 1% and typically about 0.5% by weight. We prefer to carry out the mixing, and forming of the mixture into unit doses, at a relative humidity of less than about 65%, e.g. from about 40 to 65%.

The composition preferably comprises particles of the relatively coarse carrier coated with a layer of the fine sodium cromoglycate. We have surprisingly found that we can achieve the same effect as with the so called 'ordered mixing' with many times larger proportion of fine sodium cromoglycate to carrier than would be expected from theoretical considerations. The composition also desirably is such that there is no caking of the blend between mixing and formation into unit dosages, e.g. sacheting. The mixture also desirably is such that there is no, or very little, segregation when it is filled, stored and transported.

We prefer the composition to contain no other excipients than the water soluble carrier.

The compositions of the invention can be used in the treatment of a wide variety of conditions, e.g. Crohn's disease (a condition of the small, and sometimes also of the large, intestine), atrophic gastritis (a condition of the stomach), ulcerative colitis (a condition of the rectum), proctitis (a condition of the rectum and lower large intestine), coeliac disease (a condition of the small intestine), regional ileitis (a regional inflammatory condition of the terminal ileum), peptic ulceration (a condition of the stomach and duodenum), gastrointestinal allergy (e.g. milk, gluten, food additive etc. allergy), irritable bowel syndrome and gastrointestinal bleeding induced by administration of an anti-inflammatory, e.g. indomethacin or aspirin.

The composition is particularly useful for the treatment of food allergy in children.

The compositions of the invention may be made by mixing the fine sodium cromoglycate with the coarse carrier e.g. in a planetary or a matrix mixer. Desirably a three (or greater) layer sandwich of the components is placed in the mixer before the mixing commences. The mixing should be carried out for a sufficient time to ensure as uniform a mix as possible. Mixing times of up to 60 minutes, but preferably of less than 15 minutes are generally suitable. The mixer is preferably such as not to change the particle sizes of the ingredients significantly during the mixing process.

The invention is illustrated but in no way limited by the following Examples.

EXAMPLE 1

| | | |
|---|---|---|
| Sodium cromoglycate (Apex milled mass median diameter 3–6 microns, greater than 90% less than 30 microns. Measured as 'anhydrous' material | 100 mg | 200 mg |
| Sucrose (Caster Sugar sieve cut 90% to greater than 150 microns, 90% less than 450 microns) | 1.03 g | 2.01 g |

A sandwich of sucrose-sodium cromoglycate-sucrose was placed in a matrix mixer (100L Fielder) in which a main rotor passed through the base of the powder and a side chopper rotor disrupts the mass movement of the powder. A satisfactory degree of mixing is achieved after a time of from about 2 to 10 minutes of operation of the mixer. The formulations are put up in paper/foil/polyethylene or 'Surlyn' laminate sachets; the individual sachets being 40×75 mm and produced in strips of five 160×75 mm with perforations between each. These strips are cartoned for appropriate treatment periods, e.g. 50's, 60's, 100's etc.

EXAMPLE 2

2 g Of the mixture of Example 1 when poured into 80 ml of tap water at 25° C.±3° C. in a 100 ml beaker stirred by a high speed stirrer (1200 rpm) dissolved (visual assessment) in 20–25 seconds. By way of contrast 200 mg of granules of sodium cromoglycate mean size 120 microns took 45–50 seconds to dissolve.

We claim:

1. A water-soluble composition for treatment of a condition of a gastro-intestinal tract comprising:

a particulate water-soluble pharmaceutically acceptable carrier consisting essentially of sucrose and having a particle size of 200–1000 microns; and particulate sodium cromoglycate having a mass median diameter of 2–30 microns forming a coating on said carrier particles.

the proportion of carrier to sodium cromoglycate in the coated particles being 2–20 parts by weight of carrier to 1 part of sodium cromoglycate.

2. A composition according to claim 1, wherein the sodium cromoglycate has a mass median diameter of from 2 to 10 microns, and the water soluble carrier has a particle size of from 200 to 500 microns.

3. A composition according to claim 1 containing from 5 to 12 parts by weight of sucrose for each part by weight of sodium cromoglycate.

4. A composition according to claim 1 in unit dosage form containing from 50 to 300 mg of sodium cromoglycate.

5. A composition according to claim 4 contained in a sachet made of material which will prevent the ingress of water.

6. A composition according to claim 1 containing less than 2% by weight of water.

7. A composition according to claim 1 containing no other excipient than the water soluble carrier.

8. A method for preparing a sodium cromoglycate composition having an increased rate of dissolution in cold water which comprises depositing particulate sodium cromoglycate having a mass median diameter of 2–30 microns as a surface layer on a particulate water-soluble pharmaceutically acceptable carrier having a particle size of 200–1000 microns and consisting essentially of sucrose, the proportion of carrier to sodium cromoglycate in the coated particles being 2–20 parts of weight of carrier to 1 part of sodium cromoclycate.

9. The method of claim 8 wherein the sodium cromoglycate has a mass median diameter of 2–10 microns, and the water soluble carrier has a particle size of 200–500 microns.

10. The method of claim 8 wherein the proportion of carrier to sodium cromoglycate in the coated particles is 5–12 parts by weight of carrier to 1 part of sodium cromoglycate.

* * * * *